(12) United States Patent
Vivian et al.

(10) Patent No.: US 11,623,063 B2
(45) Date of Patent: Apr. 11, 2023

(54) HUMIDIFIER WITH INGRESS PROTECTION FOR USE IN CPAP THERAPY

(71) Applicant: KONINKLIJKE PHILIPS N.V., Eindhoven (NL)

(72) Inventors: Justin Michael Vivian, Freeport, PA (US); Eric L. Holmes, Pittsburgh, PA (US); Christopher James McCracken, Harrison City, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 827 days.

(21) Appl. No.: 16/582,201

(22) Filed: Sep. 25, 2019

(65) Prior Publication Data
US 2020/0101259 A1    Apr. 2, 2020

Related U.S. Application Data

(60) Provisional application No. 62/738,306, filed on Sep. 28, 2018.

(51) Int. Cl.
*A61M 16/16*    (2006.01)
*A61M 16/20*    (2006.01)

(52) U.S. Cl.
CPC ........ *A61M 16/164* (2014.02); *A61M 16/208* (2013.01)

(58) Field of Classification Search
CPC ........... A61M 16/0057; A61M 16/0063–0081; A61M 16/14; A61M 16/16–164; A61M 16/208
See application file for complete search history.

(56) References Cited

U.S. PATENT DOCUMENTS

| | | | |
|---|---|---|---|
| 8,905,026 B2 * | 12/2014 | Grychowski | A61M 16/0816 128/205.24 |
| 2007/0157928 A1 * | 7/2007 | Pujol | A61M 16/109 261/119.1 |
| 2013/0199524 A1 | 8/2013 | Hardin | |
| 2017/0361058 A1 | 12/2017 | Gaw | |

* cited by examiner

*Primary Examiner* — Rachel T Sippel (57) ABSTRACT

An apparatus for use in humidifying a flow of treatment gas for a user includes: a housing; an inlet structured to receive the flow of treatment gas from a gas flow generator; an outlet structured to convey the flow of treatment gas to a patient interface device; a compartment defined in the housing, the compartment being structured to hold a volume of water therein; a primary valve disposed between the inlet and the compartment, the primary valve being structured to permit passage of the flow of treatment gas from the inlet to the compartment and to prevent passage of a fluid from the compartment to the inlet; and a secondary valve disposed between the compartment and the inlet which is structured to permit passage of a fluid from the compartment to the inlet and to prevent passage of the flow of treatment gas from the inlet to the compartment.

20 Claims, 5 Drawing Sheets

HUMIDIFIER WITH INGRESS PROTECTION FOR USE IN CPAP THERAPY

This application claims the benefit of U.S. Provisional Application No. 62/738,306, filed Sep. 28, 2018. This application is hereby incorporated by reference herein.

BACKGROUND OF THE INVENTION

1. Field of the Invention

The present invention pertains to humidifiers for use in airway pressure support systems for delivering a flow of a humidified gas to the airway of a patient and, more particularly to arrangements for preventing the passage of water from the inlet of such humidifiers.

2. Description of the Related Art

Many individuals suffer from disordered breathing during sleep. Sleep apnea is a common example of such sleep disordered breathing suffered by millions of people throughout the world. One type of sleep apnea is obstructive sleep apnea (OSA), which is a condition in which sleep is repeatedly interrupted by an inability to breathe due to an obstruction of the airway; typically the upper airway or pharyngeal area. Obstruction of the airway is generally believed to be due, at least in part, to a general relaxation of the muscles which stabilize the upper airway segment, thereby allowing the tissues to collapse the airway. Another type of sleep apnea syndrome is a central apnea, which is a cessation of respiration due to the absence of respiratory signals from the brain's respiratory center. An apnea condition, whether obstructive, central, or mixed, which is a combination of obstructive and central, is defined as the complete or near cessation of breathing, for example a 90% or greater reduction in peak respiratory air-flow.

Those afflicted with sleep apnea experience sleep fragmentation and complete or nearly complete cessation of ventilation intermittently during sleep with potentially severe degrees of oxyhemoglobin desaturation. These symptoms may be translated clinically into extreme daytime sleepiness, cardiac arrhythmias, pulmonary-artery hypertension, congestive heart failure and/or cognitive dysfunction. Other consequences of sleep apnea include right ventricular dysfunction, carbon dioxide retention during wakefulness, as well as during sleep, and continuous reduced arterial oxygen tension. Sleep apnea sufferers may be at risk for excessive mortality from these factors as well as by an elevated risk for accidents while driving and/or operating potentially dangerous equipment.

Even if a patient does not suffer from a complete or nearly complete obstruction of the airway, it is also known that adverse effects, such as arousals from sleep, can occur where there is only a partial obstruction of the airway. Partial obstruction of the airway typically results in shallow breathing referred to as a hypopnea. A hypopnea is typically defined as a 50% or greater reduction in the peak respiratory air-flow. Other types of sleep disordered breathing include, without limitation, upper airway resistance syndrome (UARS) and vibration of the airway, such as vibration of the pharyngeal wall, commonly referred to as snoring.

It is well known to treat sleep disordered breathing by applying a continuous positive air pressure (CPAP) to the patient's airway. This positive pressure effectively "splints" the airway, thereby maintaining an open passage to the lungs. It is also known to provide a positive pressure therapy in which the pressure of gas delivered to the patient varies with the patient's breathing cycle, or varies with the patient's breathing effort, to increase the comfort to the patient. This pressure support technique is referred to as bi-level pressure support, in which the inspiratory positive airway pressure (IPAP) delivered to the patient is higher than the expiratory positive airway pressure (EPAP). It is further known to provide a positive pressure therapy in which the pressure is automatically adjusted based on the detected conditions of the patient, such as whether the patient is experiencing an apnea and/or hypopnea. This pressure support technique is referred to as an auto-titration type of pressure support, because the pressure support device seeks to provide a pressure to the patient that is only as high as necessary to treat the disordered breathing.

Pressure support therapies as just described involve the placement of a patient interface device including a mask component having a soft, flexible sealing cushion on the face of the patient. The mask component may be, without limitation, a nasal mask that covers the patient's nose, a nasal/oral mask that covers the patient's nose and mouth, or a full face mask that covers the patient's face. Such patient interface devices may also employ other patient contacting components, such as forehead supports, cheek pads and chin pads. The patient interface device is typically secured to the patient's head by a headgear component. The patient interface device is connected to a gas delivery tube or conduit and interfaces the pressure support device with the airway of the patient, so that a flow of breathing gas can be delivered from the pressure/flow generating device to the airway of the patient.

Humidifiers are frequently provided between or integral with a PAP machine and the user interface in order to humidify the otherwise relatively-dry compressed air generated by the PAP machine. A humidifier generally consists of a heated tank of water with air blown over the water's surface to be humidified to the desired level. The tank of water is generally heated via a heater plate located below a metal pan in the bottom of the tank. The tank of water is heated to a temperature calculated to provide the desired humidity output. During patient inhalation, the air travels from the CPAP, through the humidifier (picking up moisture), and then out the therapy circuit to the patient. On exhalation, air travels through the therapy circuit, back through the humidifier water chamber, through the CPAP and out to atmosphere.

On these devices, the water chamber is generally much larger than the volume of water they contain. This is done to allow for operation of the humidifier when tilted up to 20° in all directions so that no water is leaked into the patient tube or into the CPAP device that the humidifier is attached.

The use of a humidifier along with CPAP therapy can increase compliance of a patient by providing additional comfort with the addition of humidification. When humidification is used along with CPAP therapy, there is a need to prevent the water used in the humidifier from flowing back into the CPAP device. Such water ingress into a CPAP device from a humidifier can cause catastrophic issues to the electronics and motor blower of the device. More importantly water inside the CPAP unit where electricity is present can create a potential safety issue. Under normal use, when the CPAP and humidifier are operated within their recommended orientations, water ingress will not present an issue. Furthermore, when the humidifier is properly filled with water using the proper manufacturers instruction, there should not be an issue with water ingress into the CPAP device. The issue of water ingress mainly occurs during normal mis-use case scenarios like overfilling the humidifier past the maximum fill requirement of the manufacturer. Another common mis-use case scenario that can create water ingress issues is when the user of the device does not empty the water out of the humidifier and then moves the device and or travels with it.

Currently the most common method used for water ingress protection on a CPAP humidifier system is what is referred to as volumetric water ingress protection. The way that this method works is by providing a sufficient amount of volume within the water chamber so that there is enough total volume to be able to rotate the humidifier 360 degrees without the water from the chamber flowing back into the CPAP device. This method is extremely effective in providing water ingress protection for the CPAP device but the problem or disadvantage is that a large amount of volume and typically overall height of the system is needed in order to use this method of water protection.

SUMMARY OF THE INVENTION

Embodiments of the present invention solve or overcome the disadvantages or problems of the commonly used method above by eliminating the need for a large volume tank which is needed in order to achieve effective volumetric water ingress protection. Without the need for a large volume tank, more design flexibility is achieved and smaller lower profile systems can be used while still maintaining 360-degree water ingress protection. The way in which this works is two valves are used, the first and larger of the two valves is used in the primary flow path where the CPAP therapy is provided. This valve is normally closed and opens when the device is providing therapy. This valve serves as the systems main water ingress protection mechanism by closing off the air-path between the humidifier and CPAP when the device therapy is off, therefore not allowing water to enter the CPAP device.

One problem with using a mechanical valve that closes off the air-path between the humidifier and CPAP is that under low pressure/low flow therapy conditions, the primary valve can become closed during the patient expiratory phase. When this valve is closed while therapy is still being provided, the expiratory phase of the patient can become very resistant and somewhat uncomfortable. The use of a secondary one-way valve between the main therapy valve and the connection to the CPAP solves this issue. This valve's primary function is to open when the therapy valve is closed and provide exhalation relief to the patient by allowing flow from the patient expiratory phase to enter the air-path of the device.

Another problem with using a single mechanical valve for water ingress protection is that when the valve is submerged in water when the humidifier is rotated or turned to an orientation to submerge it, the valve will start to flutter to try an allow air to enter the air-path of the device. This occurs due to the pressure differential that happens when the flow-path is submerged in water and the valve is closed. The problem that occurs when the valve flutters is that water will enter into the flow-path and eliminate the effectiveness of the water protection measures of the main valve. The secondary one-way valve eliminates this problem by providing a path for air to enter into the flow path without compromising the water ingress protection of the main valve.

As one aspect of the disclosed concept, an apparatus for use in humidifying a flow of treatment gas for providing to a user, the apparatus comprises: a housing; an inlet structured to receive the flow of treatment gas from a gas flow generator; an outlet structured to convey the flow of treatment gas to a patient interface device; a compartment defined in the housing, the compartment being structured to hold a volume of water therein; a primary valve disposed between the inlet and the compartment, the primary valve being structured to permit passage of the flow of treatment gas from the inlet to the compartment and to prevent passage of a fluid from the compartment to the inlet; and a secondary valve disposed between the compartment and the inlet, the secondary valve being structured to permit passage of a fluid from the compartment to the inlet and to prevent passage of the flow of treatment gas from the inlet to the compartment.

The primary valve may comprise a flapper valve.

The secondary valve may comprise a duckbill valve.

The secondary valve may comprise a flapper valve.

The apparatus may further comprise an elongated passage extending between the secondary valve and a distal end disposed at or about the outlet, wherein the elongated passage is structured to convey the fluid from the outlet to the secondary valve without exposing the fluid to the volume of water.

As another aspect of the disclosed concept, a device for use in providing a humidified flow of a treatment gas to the airway of a user comprises: a housing; a flow generating device disposed in the housing, the flow generating device structured to produce the flow of the treatment gas; and an apparatus disposed in the housing for humidifying the flow of the treatment gas. The apparatus comprises: an inlet structured to receive the flow of treatment gas from the flow generating device; an outlet structured to convey the flow of treatment gas; a compartment defined in the housing, the compartment being structured to hold a volume of water therein; a primary valve disposed between the inlet and the compartment, the primary valve being structured to permit passage of the flow of treatment gas from the inlet to the compartment and to prevent passage of a fluid from the compartment to the inlet; and a secondary valve disposed between the compartment and the inlet, the secondary valve being structured to permit passage of a fluid from the compartment to the inlet and to prevent passage of the flow of treatment gas from the inlet to the compartment.

The housing may comprise a first housing and a second housing selectively coupled to the first housing; wherein the flow generating device is disposed in the first housing; and wherein the apparatus is disposed in the second housing. The primary valve may comprise a flapper valve. The secondary valve may comprise a duckbill valve. The secondary valve may comprise a flapper valve.

The apparatus may further comprise an elongated passage extending between the secondary valve and a distal end disposed at or about the outlet, wherein the elongated passage is structured to convey the fluid from the outlet to the secondary valve without exposing the fluid to the volume of water.

As another aspect of the present invention, a system for providing a humidified flow of a treatment gas to the airway of a user comprises a device structured to provide a humidified flow of a treatment gas. The device comprises: a housing; a flow generating device disposed in the housing, the flow generating device structured to produce the flow of the treatment gas; and an apparatus disposed in the housing for humidifying the flow of the treatment gas. The apparatus comprises: an inlet structured to receive the flow of treatment gas from the flow generating device; an outlet structured to convey the flow of treatment gas; a compartment defined in the housing, the compartment being structured to hold a volume of water therein; a primary valve disposed between the inlet and the compartment, the primary valve being structured to permit passage of the flow of treatment gas from the inlet to the compartment and to prevent passage of a fluid from the compartment to the inlet; and a secondary valve disposed between the compartment and the inlet, the secondary valve being structured to permit passage of a fluid from the compartment to the inlet and to prevent passage of the flow of treatment gas from the inlet to the compartment. The system further comprises a delivery conduit having a first end coupled to the outlet of the apparatus and an opposite second end; and a patient interface device coupled to the second end of the conduit, wherein the conduit is structured to convey the flow of treatment gas from the outlet to the patient interface device.

The housing may comprise a first housing and a second housing selectively coupled to the first housing; wherein the flow generating device is disposed in the first housing; and wherein the apparatus is disposed in the second housing.

The primary valve may comprise a flapper valve. The secondary valve may comprise a duckbill valve. The secondary valve may comprise a flapper valve.

The apparatus may further comprise an elongated passage extending between the secondary valve and a distal end disposed at or about the outlet, wherein the elongated passage is structured to convey the fluid from the outlet to the secondary valve without exposing the fluid to the volume of water.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF EXEMPLARY EMBODIMENTS

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are coupled directly in contact with each other. As used herein, "fixedly coupled" or "fixed" means that two components are coupled so as to move as one while maintaining a constant orientation relative to each other. As used herein, "selectively coupled" means that two elements are coupled in a manner in which the two elements may be readily uncoupled or recoupled.

As used herein, the word "unitary" means a component is created as a single piece or unit. That is, a component that includes pieces that are created separately and then coupled together as a unit is not a "unitary" component or body. As used herein, the statement that two or more parts or components "engage" one another shall mean that the parts exert a force against one another either directly or through one or more intermediate parts or components. As used herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
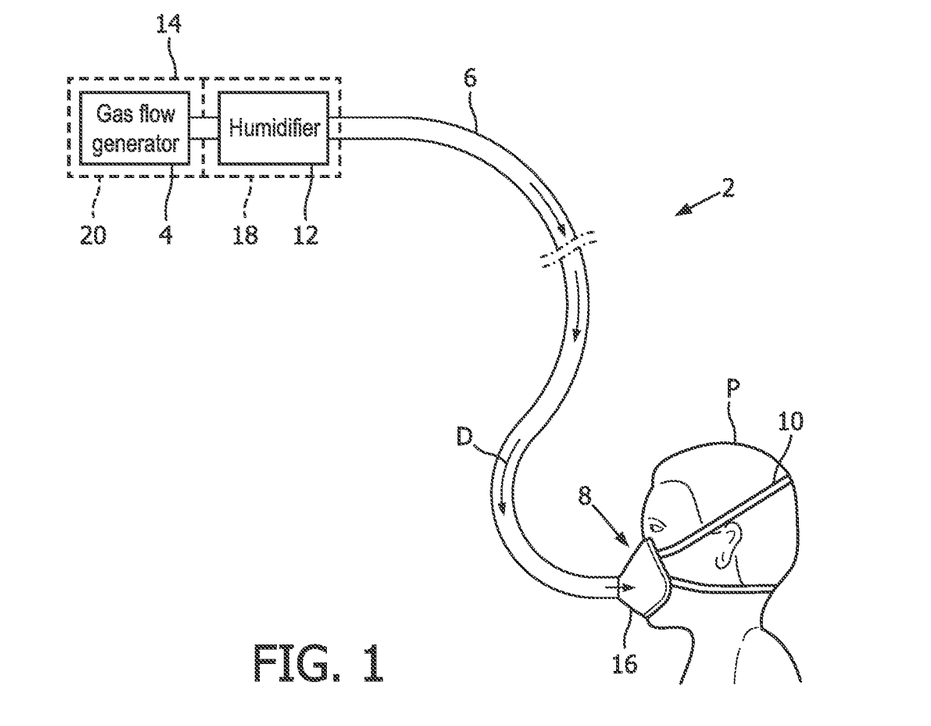
FIG. 1 is a schematic diagram of an airway pressure support system according to one particular, non-limiting embodiment in which the present invention in its various embodiments may be implemented, shown with a patient interface device thereof disposed on the face of a patient.

FIG. 1 is a schematic diagram of an airway pressure support system 2 according to one particular, non-limiting embodiment in which the present invention in its various embodiments may be implemented. Pressure support system 2 includes a gas flow generator 4, a delivery conduit 6, a patient interface device 8 structured to engage about an airway of the patient, and a headgear 10 for securing patient interface device 8 to the head of a patient (P). Gas flow generator 4 is structured to generate a flow of breathing gas to be delivered through patient interface device 8 to the airway of patient P. The flow of breathing gas may be heated and/or humidified by a humidifier 12 which may be: provided in a common housing 14 with gas flow generator 4 (such as shown in dashed line in FIG. 1); provided in a separate housing 18 which is selectively coupleable to a housing 20 of gas flow generator 4; or provided in housing 18 which is separate from, and spaced a distance from, housing 20 of gas flow generator 4. In other words, housings 18 and 20 may be formed as a single housing 14, as two separate units which may be selectively coupled and uncoupled with each other, or as two separate units which are spaced apart and coupled generally only via a suitable conduit.

Gas flow generator 4 may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pa.), and auto-titration pressure support devices. Delivery conduit 6 is structured to communicate the flow of breathing gas from gas flow generator 4 to patient interface device 8. Delivery conduit 6 and patient interface device 8 are often collectively referred to as a patient circuit.

A BiPAP® device is a bi-level device in which the pressure provided to the patient varies with the patient's respiratory cycle, so that a higher pressure is delivered during inspiration than during expiration. An auto-titration pressure support system is a system in which the pressure varies with the condition of the patient, such as whether the patient is snoring or experiencing an apnea or hypopnea. The present invention contemplates that gas flow generator 4 is any conventional system for delivering a flow of gas to an airway of a patient or for elevating a pressure of gas at an airway of the patient, including the pressure support systems summarized above and non-invasive ventilation systems. Although described herein in example embodiments wherein a pressurized flow of gas is utilized, it is to be appreciated that embodiments of the invention as described herein could also be readily employed in other generally non-pressurized applications (e.g., without limitation, in high flow therapy applications).

In the exemplary embodiment shown in FIG. 1, patient interface device 8 includes a patient sealing assembly 16, which in the illustrated embodiment is a full face mask. It is to be appreciated, however, that other types of patient sealing assemblies, such as, without limitation, a nasal/oral mask, a nasal cushion, or any other arrangements which facilitate the delivery of the flow of breathing gas to the airway of a patient may be substituted for patient sealing assembly 16 while remaining within the scope of the present invention. It is also to be appreciated that headgear 10 is provided solely for exemplary purposes and that any suitable headgear arrangement may be employed without varying from the scope of the present invention.

Figure 2A:
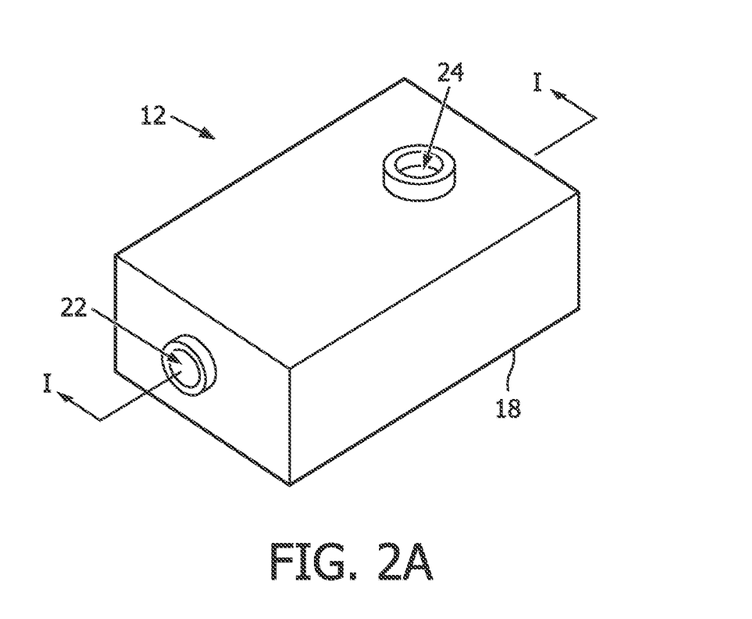
FIG. 2A is a schematic isometric view of an apparatus for humidifying a flow of treatment gas according to one particular, non-limiting embodiment of the present invention.
Figure 2B:
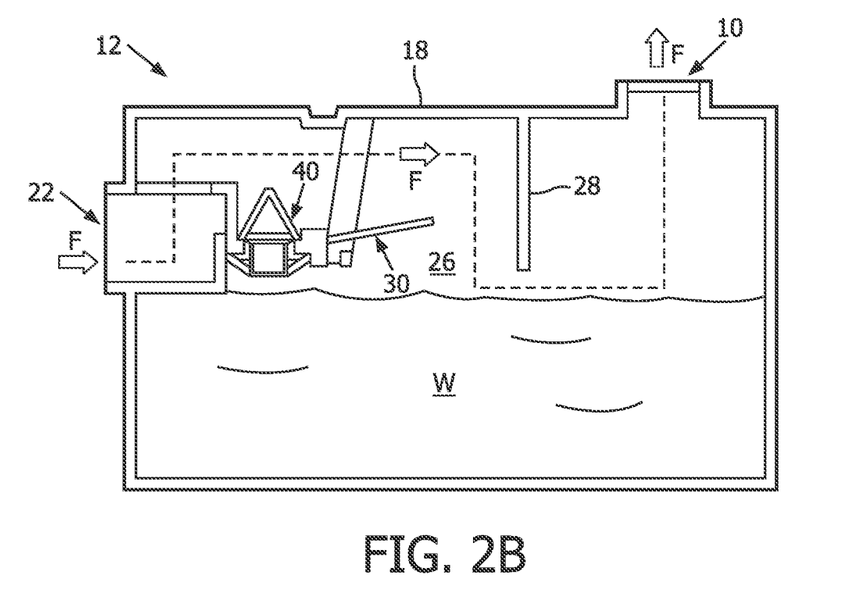
FIG. 2B is a schematic sectional view of the apparatus of FIG. 2A taken along line I-I of FIG. 2A shown with internal components thereof disposed in a first positioning corresponding to when a flow of treatment gas is being received by a user of the apparatus.
Figure 2C:
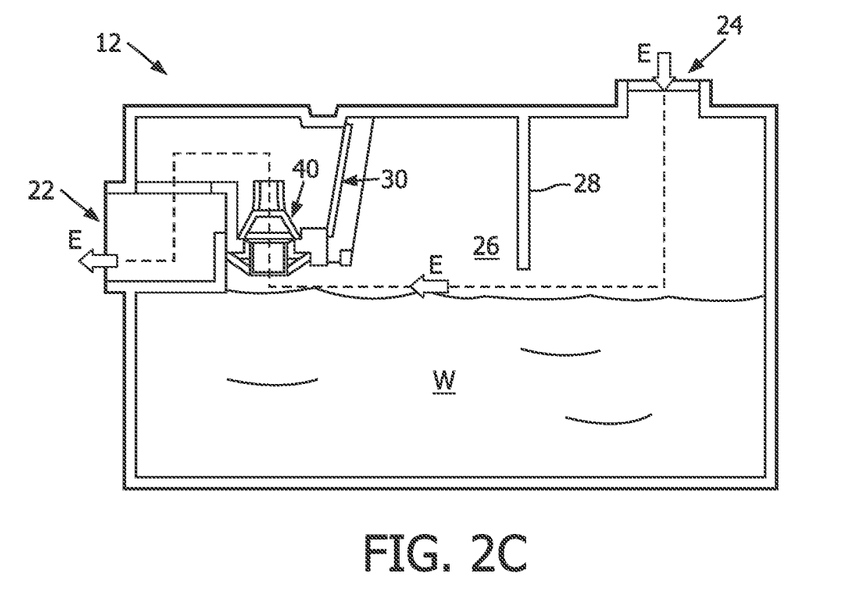
FIG. 2C is a schematic sectional view of the apparatus of FIG. 2A taken along I-I of FIG. 2A shown with internal components thereof disposed in a second positioning corresponding to when a user of the apparatus is exhaling.

Referring to FIGS. 2A-2C, humidifier 12 includes: an inlet 22 which is structured to receive a flow of treatment gas (shown by arrows F and the associated broken line in FIG. 2B) produced by gas flow generator 4; an outlet 24 which is structured to convey the flow of treatment gas F to the patient; and a compartment 26 which is structured to house a volume of water W therein for humidifying the flow of treatment gas F passing through housing 18 and compartment 26 thereof from inlet 22 to outlet 24. In the example illustrated in FIGS. 2B and 2C, a baffle 28 which extends generally downward into compartment 26 from a top wall thereof is provided to encourage interaction of the flow of treatment gas F with the volume of water W.

Humidifier 12 further includes a primary valve 30 disposed between inlet 22 and compartment 26. Primary valve 30 is a one-way valve which is moveable between an open position (FIG. 2B), in which primary valve 30 is structured to permit passage of the flow of treatment gas F from inlet 22 to compartment 26, and a closed position (FIG. 2C) in which primary valve 30 is structured to prevent passage of a fluid or fluids (e.g., air, water, etc.) from compartment 26 to inlet 22. Primary valve 30 is normally disposed in a closed position except for when adequate pressure is acting thereon to open primary valve 30. In one example embodiment of the present invention, primary valve 30 is a flapper valve which is structured to be disposed in an open position when a flow of treatment gas F is provided through humidifier 12 to a patient in the pressure range of 4 cmH2O to 25 cmH2O at a flow rate of 0-100 LPM. Conversely, in such example embodiment, primary valve 30 is structured to be disposed in a closed position when the aforementioned flow rate of the aforementioned flow of treatment gas F drops to a flowrate in the range of 0 to −80 LPM, such as when a patient receiving the treatment exhales exhalation gases, such as shown by arrows E (and the associated broken line) in FIG. 2C and described further below.

Continuing to refer to FIGS. 2B and 2C, humidifier 12 further includes a secondary valve 40 disposed between compartment 26 and inlet 22. Secondary valve 40 is a one-way valve which is moveable between an open position (FIG. 2C), in which secondary valve 40 is structured to permit passage of a fluid, such as exhalation gases E from compartment 26 to inlet 22, and a closed position (FIG. 2B) in which secondary valve 40 is structured to prevent passage of a fluid or fluids, such as flow of treatment gas F, from inlet 22 to compartment 26. Secondary valve 40 is normally disposed in a closed position except for when adequate pressure is acting thereon to open secondary valve 40. In one example embodiment of the present invention, secondary valve 40 is a duckbill valve which is structured to be disposed in an open position when primary valve 30 is closed and the pressure in compartment 26 is greater than the pressure in inlet 22.

Secondary valve 40 is needed to relieve expiratory flow during the exhalation cycle of CPAP therapy. Secondary valve 40 is needed in order to have effective water ingress protection (i.e., to keep water from exiting humidifier 12 via inlet 22). The placement of secondary valve 40 is critical to the function of the two valve system. Secondary valve 40 is preferably placed between primary valve 30 and inlet 22 of humidifier 12. Preferably, secondary valve 40 is also placed in an orientation where it is difficult to submerge in water when the device is rotated 360 degrees so that the system can be properly vented as previously described.

From the foregoing description of humidifier 12, it is thus to be appreciated that during a CPAP treatment, primary valve 30 is generally disposed in an open position with the flow of treatment gas F passing into humidifier 12 via inlet 22, passing through primary valve 30, being directed generally toward water W by baffle 28, then exiting from chamber 26 and humidifier 12 via outlet 24, and then passing onward to the patient. However, when a patient is exhaling, the resulting pressure/flow causes primary valve 30 to return to a closed position and secondary valve 40 to open, thus allowing the flow of exhalation gases E entering humidifier 12 via outlet 24 to pass through humidifier 12 and exit via inlet 22. When a CPAP treatment is not occurring, both primary valve 30 and secondary valve 40 are disposed in closed positions, thus preventing any water W from exiting chamber 26, and thus preventing any water from exiting inlet 22.

Referring now to FIGS. 3A-3D, a humidifier 112 in accordance with another example embodiment of the invention which may be employed in system 2 of FIG. 1 is shown. Humidifier 112 includes: an inlet 122 which is structured to receive a flow of treatment gas (shown by arrows F in FIG. 3B) produced by a gas flow generator, such a gas flow generator 4 previously discussed; an outlet 124 which is structured to convey the flow of treatment gas F; and a compartment 126 which is structured to house a volume of water W therein for humidifying the flow of treatment gas F passing through housing 118 and compartment 126 thereof from inlet 122 to outlet 124. In the example illustrated in FIGS. 3B-3D, a baffle 128 which extends generally downward into compartment 126 from a top wall thereof is provided to encourage interaction of the flow of treatment gas F with the volume of water W.

Humidifier 112 further includes a primary valve 130 disposed between inlet 122 and compartment 126. Primary valve 130 is a one-way valve which is moveable between an open position (FIG. 3B), in which primary valve 130 is structured to permit passage of the flow of treatment gas F from inlet 122 to compartment 126, and a closed position (FIG. 3C) in which primary valve 130 is structured to prevent passage of a fluid or fluids (e.g., air, water, etc.) from compartment 126 to inlet 122. In one example embodiment of the present invention, primary valve 130 is a flapper valve which is structured to be disposed in an open position when a flow of treatment gas F is provided through humidifier 112 to a patient in the pressure range of 4 cmH2O to 25 cmH2O at a flow rate of 0-100 LPM. Conversely, in such example embodiment, primary valve 130 is structured to be disposed in a closed position when the aforementioned flow rate of the aforementioned flow of treatment gas F drops to a flowrate in the range of 0 to −80 LPM, such as when a patient receiving the treatment exhales exhalation gases, such as shown by arrows E in FIG. 3C and described further below.

Figure 3A:
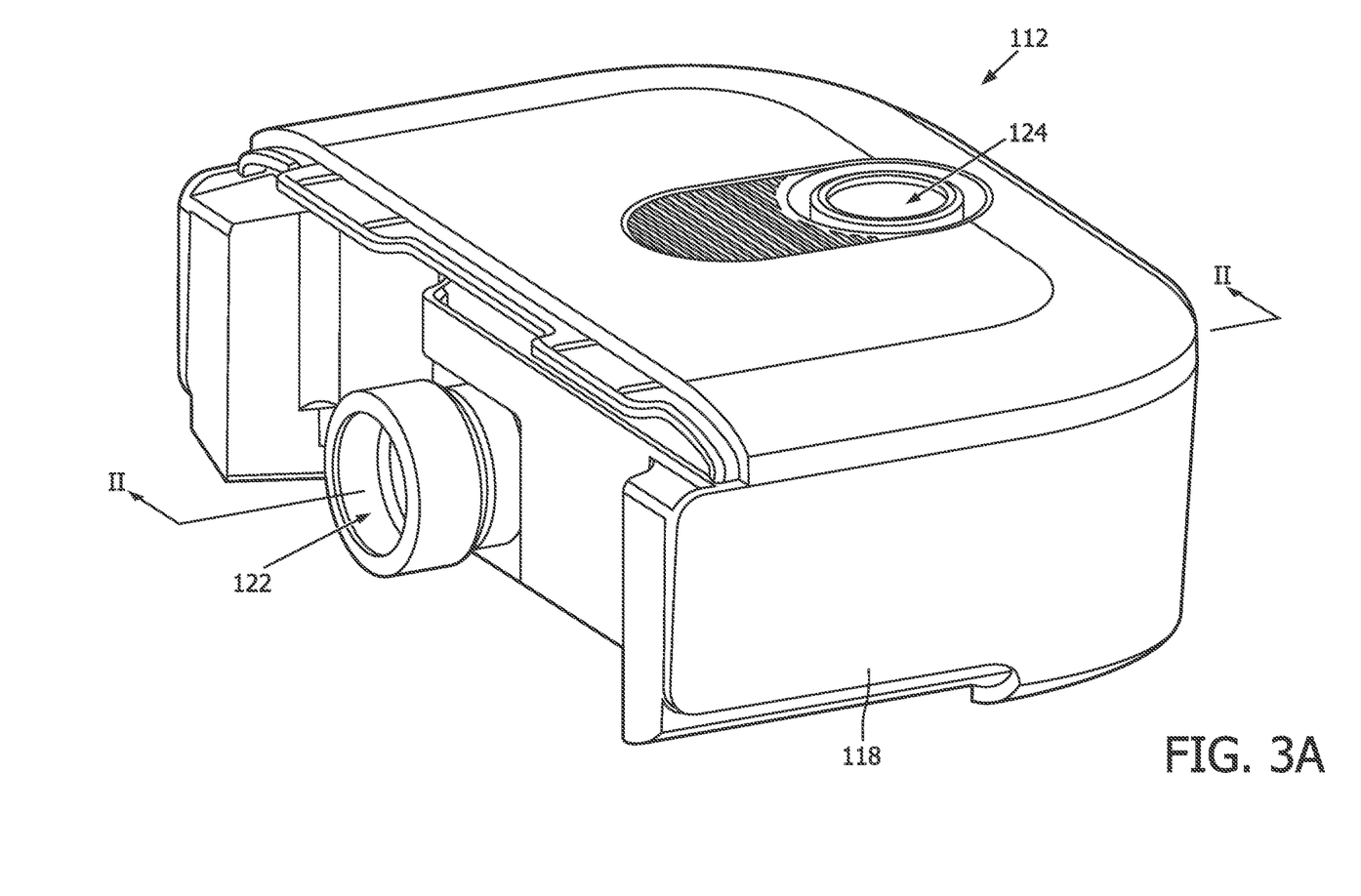
FIG. 3A is a schematic isometric view of an another apparatus for humidifying a flow of treatment gas according to one particular, non-limiting embodiment of the present invention.
Figure 3B:
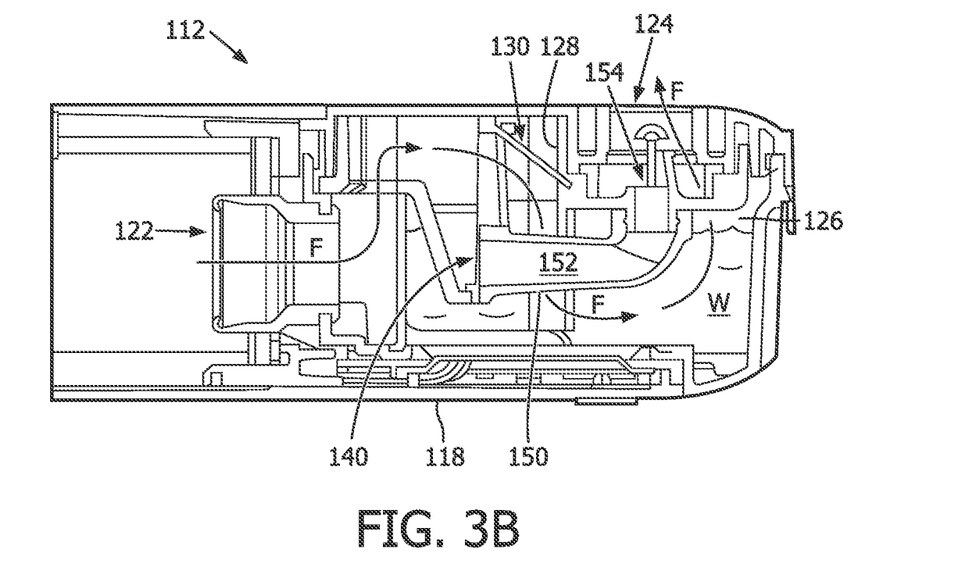
FIG. 3B is a schematic sectional view of the apparatus of FIG. 3A taken along line II-II of FIG. 3A shown with internal components thereof disposed in a first positioning corresponding to when a flow of treatment gas is being received by a user of the apparatus.
Figure 3C:
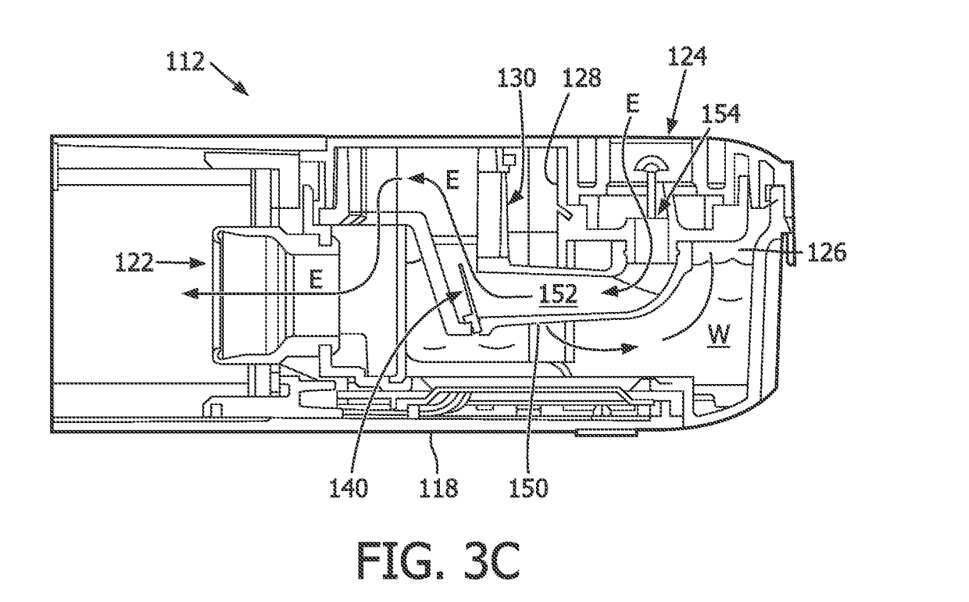
FIG. 3C is a schematic sectional view of the apparatus of FIG. 3A taken along line II-II shown with internal components thereof disposed in a second positioning corresponding to when a user of the apparatus is exhaling.
Figure 3D:
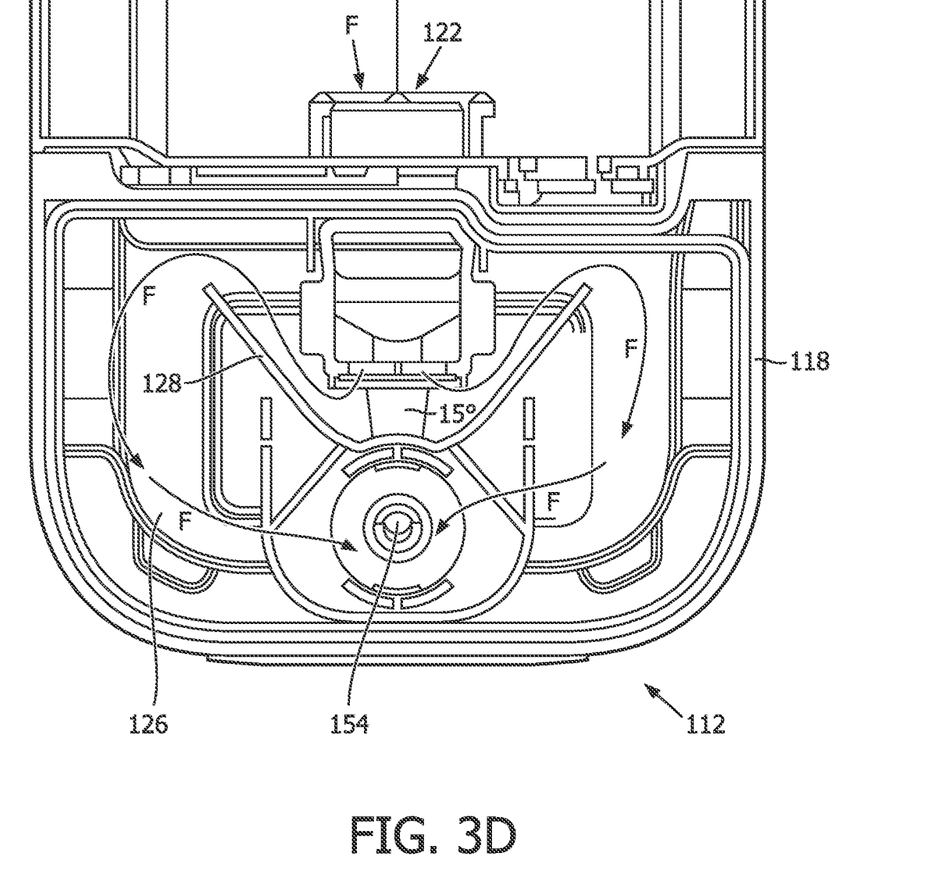
FIG. 3D is a top vie of the apparatus of FIG. 3A shown with a top cover thereof removed to show internal details.

Continuing to refer to FIGS. 3B and 3C, humidifier 112 further includes a secondary valve 140 disposed between compartment 126 and inlet 122. Secondary valve 140 is a one-way valve which is moveable between an open position (FIG. 3C), in which secondary valve 140 is structured to permit passage of a fluid, such as exhalation gases E from compartment 126 to inlet 122, and a closed position (FIG. 3B) in which secondary valve 140 is structured to prevent passage of a fluid or fluids, such as flow of treatment gas F, from inlet 122 to compartment 126.

In one example embodiment of the present invention, secondary valve 140 is a flapper valve which is structured to be disposed in a closed position when primary valve 130 is open, and structured to be disposed in an open position when the pressure in compartment 126 is greater than the pressure in inlet 122. Secondary valve 140 is needed to prevent therapy flow in the positive direction from traveling through bypass tube 150 and out outlet 124, thus bypassing the humidifier and reducing humidification output.

In order to reduce and/or eliminate loss of water W from compartment 126 through secondary valve 140 during exhalation, humidifier 112 further includes a bypass tube 150 which defines an elongated passage 152 therein. Elongated passage 152 extends between secondary valve 140 and a distal opening 154 of bypass tube 150 disposed at or about outlet 124. In the example embodiment illustrated in FIGS. 3B-3D, distal opening 154 is generally aligned (i.e., disposed along a common central axis) with outlet 124. Such positioning of distal opening 154 near inlet outlet 124 generally eliminates interaction between exhalation gases E and the water W inside chamber 126 as exhalation gases E are not generally exposed to the water W therein.

From the foregoing description of humidifier 112, it is thus to be appreciated that during a CPAP treatment, primary valve 130 is generally disposed in an open position with the flow of treatment gas F passing into humidifier 112 via inlet 122, passing through primary valve 130, being directed generally toward water W by baffle 128 (and around bypass tube 150), then exiting from chamber 126 and humidifier 112 upward away from distal opening 154 via outlet 124, and passing onward to the patient. However, when a patient is exhaling, the resulting pressure/flow causes primary valve 130 to return to a closed position and secondary valve 140 to open as the flow of exhalation gases E entering humidifier 112 via outlet 124 immediately enter distal opening 154 of bypass tube 150, pass through bypass tube 150 and secondary valve 140, and exit humidifier 112 via inlet 22. When a CPAP treatment is not occurring, both primary valve 130 and secondary valve 140 are disposed in closed positions, thus preventing any water W from exiting chamber 126, and thus preventing any water from exiting inlet 122.

From the foregoing examples it is to be appreciated that embodiments of the present invention overcome disadvantages or problems of the prior arrangements by eliminating the need for a large volume tank which was previously needed in order to achieve effective volumetric water ingress protection. By eliminating the need for a large volume tank, more design flexibility is achieved and smaller lower profile systems can be used while still maintaining 360-degree water ingress protection.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

What is claimed is:

1. An apparatus for use in humidifying a flow of treatment gas for providing to a user, the apparatus comprising:
   a housing;
   an inlet structured to receive the flow of treatment gas from a gas flow generator;
   an outlet structured to convey the flow of treatment gas to a patient interface device;
   a compartment defined in the housing, the compartment being structured to hold a volume of water therein;
   a primary valve disposed between the inlet and the compartment, the primary valve being in a normally closed position and structured to open and permit passage of the flow of treatment gas from the inlet to the compartment and to close and prevent passage of a fluid from the compartment to the inlet;

a secondary valve disposed between the compartment and the inlet, further in a location between the primary valve and the inlet, the secondary valve being in a normally closed position and structured to open and permit passage of the fluid from the compartment to the inlet and to close and prevent passage of the flow of treatment gas from the inlet to the compartment; and a baffle disposed downward into the compartment from a top wall of the compartment, located between (i) both the primary and secondary valves on one side and (ii) the outlet on an opposite side, the baffle configured to encourage interaction of the flow of treatment gas with the volume of water.

2. The apparatus of claim 1, wherein the primary valve comprises a flapper valve.

3. The apparatus of claim 1, wherein the secondary valve comprises a duckbill valve.

4. The apparatus of claim 1, wherein the secondary valve comprises a flapper valve.

5. The apparatus of claim 4, wherein the apparatus further comprises an elongated passage extending between the secondary valve and a distal end disposed at or about the outlet, wherein the elongated passage is structured to convey the fluid from the outlet to the secondary valve without exposing the fluid to the volume of water.

6. The apparatus of claim 1, wherein the primary valve is further structured to open and permit passage of the flow of treatment gas from the inlet to the compartment when the flow of treatment gas is provided through the inlet in a pressure range of 4 cmH$_2$O to 25 cmH$_2$O at a flow rate of 0-100 LPM and to close and prevent passage of a fluid from the compartment to the inlet when the flow of treatment gas drops in pressure less than the range of 4 cmH$_2$O to 25 cmH$_2$O at a flowrate in a range of 0-80 LPM, and wherein the secondary valve is further structured to open and permit passage of the fluid from the compartment to the inlet when pressure in the compartment is greater than pressure in the inlet and to close and prevent passage of the flow of treatment gas from the inlet to the compartment.

7. The apparatus of claim 1, wherein the primary valve is larger than the secondary valve.

8. The apparatus of claim 1, wherein both primary valve and secondary valve being disposed in the closed positions prevent any water from exiting the compartment and from exiting the inlet when a continuous positive air pressure treatment with the flow of treatment gas is not occurring.

9. A device for use in providing a humidified flow of a treatment gas to the airway of a user, the device comprising:
a housing;
a flow generating device disposed in the housing, the flow generating device structured to produce the flow of the treatment gas; and
an apparatus disposed in the housing for humidifying the flow of the treatment gas, the apparatus comprising:
an inlet structured to receive the flow of treatment gas from the flow generating device;
an outlet structured to convey the flow of treatment gas;
a compartment defined in the housing, the compartment being structured to hold a volume of water therein;
a primary valve disposed between the inlet and the compartment, the primary valve being in a normally closed position and structured to open and permit passage of the flow of treatment gas from the inlet to the compartment when the flow of treatment gas is provided through the inlet in a pressure range of 4 cmH$_2$O to 25 cmH$_2$O at a flow rate of 0-100 LPM and to close and prevent passage of a fluid from the compartment to the inlet when the flow of treatment gas drops in pressure less than the range of 4 cmH$_2$O to 25 cmH$_2$O at a flowrate in a range of 0-80 LPM;

a secondary valve disposed between the compartment and the inlet, further in a location between the primary valve and the inlet, the secondary valve being in a normally closed position and structured to open and permit passage of the fluid from the compartment to the inlet and to close and prevent passage of the flow of treatment gas from the inlet to the compartment, wherein both primary valve and secondary valve being disposed in the closed positions prevent any water from exiting the compartment and from exiting the inlet when a continuous positive air pressure treatment with the flow of treatment gas is not occurring; and a baffle disposed downward into the compartment from a top wall of the compartment, located between (i) both the primary and secondary valves on one side and (ii) the outlet on the other side, the baffle configured to encourage interaction of the flow of treatment gas with the volume of water.

10. The device of claim 9, wherein the housing comprises a first housing and a second housing selectively coupled to the first housing;
wherein the flow generating device is disposed in the first housing; and
wherein the apparatus is disposed in the second housing.

11. The device of claim 9, wherein the primary valve comprises a flapper valve.

12. The device of claim 9, wherein the secondary valve comprises a duckbill valve.

13. The device of claim 9, wherein the secondary valve comprises a flapper valve.

14. The device of claim 13, wherein the apparatus further comprises an elongated passage extending between the secondary valve and a distal end disposed at or about the outlet, wherein the elongated passage is structured to convey the fluid from the outlet to the secondary valve without exposing the fluid to the volume of water.

15. A system for providing a humidified flow of a treatment gas to the airway of a user, the system comprising:
a device structured to provide a humidified flow of a treatment gas, the device comprising:
a housing;
a flow generating device disposed in the housing, the flow generating device structured to produce the flow of the treatment gas; and
an apparatus disposed in the housing for humidifying the flow of the treatment gas, the apparatus comprising:
an inlet structured to receive the flow of treatment gas from the flow generating device;
an outlet structured to convey the flow of treatment gas;
a compartment defined in the housing, the compartment being structured to hold a volume of water therein;
a primary valve disposed between the inlet and the compartment, the primary valve being in a normally closed position and structured to open and permit passage of the flow of treatment gas from the inlet to the compartment and to close and prevent passage of a fluid from the compartment to the inlet;

a secondary valve disposed between the compartment and the inlet, further in a location between the primary valve and the inlet, the secondary valve being in a normally closed position and structured to open and permit passage of the fluid from the compartment to the inlet and to close and prevent passage of the flow of treatment gas from the inlet to the compartment, wherein both primary valve and secondary valve being disposed in the closed positions prevent any water from exiting the compartment and from exiting the inlet when a continuous positive air pressure treatment with the flow of treatment gas is not occurring; and a baffle disposed downward into the compartment from a top wall of the compartment, located between (i) both the primary and secondary valves on one side and (ii) the outlet on an opposite side, the baffle configured to encourage interaction of the flow of treatment gas with the volume of water a delivery conduit having a first end coupled to the outlet of the apparatus and an opposite second end; and a patient interface device coupled to the second end of the conduit, wherein the conduit is structured to convey the flow of treatment gas from the outlet to the patient interface device.

16. The system of claim 15, wherein the housing comprises a first housing and a second housing selectively coupled to the first housing;

wherein the flow generating device is disposed in the first housing; and wherein the apparatus is disposed in the second housing.

17. The system of claim 15, wherein the primary valve comprises a flapper valve.

18. The system of claim 15, wherein the secondary valve comprises a duckbill valve.

19. The system of claim 15, wherein the secondary valve comprises a flapper valve.

20. The system of claim 19, wherein the apparatus further comprises an elongated passage extending between the secondary valve and a distal end disposed at or about the outlet, wherein the elongated passage is structured to convey the fluid from the outlet to the secondary valve without exposing the fluid to the volume of water.

* * * * *